(12) United States Patent
Koninckx

(10) Patent No.: US 6,428,500 B1
(45) Date of Patent: *Aug. 6, 2002

(54) ADHESION PREVENTION AND AN ENDOSCOPIC INSUFFLATION SYSTEM THEREFOR

(75) Inventor: Robert Koninckx, Leuven (BE)

(73) Assignee: Saturnus AG, Luxembourg (LU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,192

(22) PCT Filed: May 7, 1998

(86) PCT No.: PCT/EP98/02829
§ 371 (c)(1),
(2), (4) Date: Jan. 20, 2000

(87) PCT Pub. No.: WO98/50064
PCT Pub. Date: Nov. 12, 1998

(30) Foreign Application Priority Data

May 7, 1997 (EP) .............................................. 97201358

(51) Int. Cl.[7] ............................................... A61M 37/00
(52) U.S. Cl. ............................................ 604/26; 604/28
(58) Field of Search ............................... 604/23–26, 28, 604/500, 505, 506, 264; 128/898; 606/185, 213

(56) References Cited

U.S. PATENT DOCUMENTS

| | | | | |
|---|---|---|---|---|
| 4,464,169 A | * | 8/1984 | Semm ........................ 604/26 |
| 5,246,419 A | * | 9/1993 | Absten ........................ 604/26 |
| 5,411,474 A | * | 5/1995 | Ott et al. ..................... 604/26 |
| 5,411,988 A | | 5/1995 | Bockow et al. | |
| 5,478,837 A | | 12/1995 | Rodgers et al. | |
| 5,534,261 A | | 7/1996 | Rodgers et al. | |
| 5,537,993 A | * | 7/1996 | Reichert et al. ........ 128/203.14 |
| 5,558,668 A | | 9/1996 | Lankford et al. | |
| 5,578,305 A | | 11/1996 | Franz et al. | |
| 6,051,241 A | * | 4/2000 | Briend et al. ............... 424/400 |

FOREIGN PATENT DOCUMENTS

| | | |
|---|---|---|
| EP | 0 369 764 | 5/1990 |
| EP | 0 712 635 | 5/1996 |
| WO | 94/00484 | 1/1994 |
| WO | 96/29987 | 10/1996 |
| WO | 96/40090 | 12/1996 |

* cited by examiner

Primary Examiner—Brian L. Casler
Assistant Examiner—Jennifer Maynard
(74) Attorney, Agent, or Firm—Banner & Witcoff, Ltd.

(57) ABSTRACT

A method of treating or preventing adhesion formation following a surgical procedure comprising administering to a patient in need thereof a medicament comprising a gas mixture comprising $O_2$ wherein the $O_2$ is present in a volume ratio from 1 to 20% and in an amount effective to treat or prevent adhesion. An endoscopic insufflation system having an insufflation line comprising gas supplying means wherein the supplying means supply a gas mixture comprising $O_2$ in a volume ratio from 1 to 20% and in an amount effective to treat or prevent adhesion formation in a patient following a surgical procedure and further comprising means for moistening the insufflation gas, means for the control of the temperature of the gas, or both.

9 Claims, 4 Drawing Sheets

ADHESION PREVENTION AND AN ENDOSCOPIC INSUFFLATION SYSTEM THEREFOR

FIELD OF THE INVENTION

The present invention relates to adhesion prevention in general and to compounds, an endoscopic insufflation system and to a method for preventing adhesion formation in particular.

BACKGROUND OF THE INVENTION

Adhesion formation is a major problem following surgical procedures and is a frequent cause of postoperative pain and of infertility. Adhesions are the major cause of intestinal obstruction and it is estimated that following an intra-abdominal procedure, adhesions occur in some 50 to 80 percent of patients.

The mechanism of adhesion formation can be summarized as follows: a trauma of the peritoneal lining is rapidly followed by an inflammatory reaction; exudation of plasma, and deposition of a fibrin matrix. Subsequently the lesion is healed by the degradation of the fibrin deposition, and by proliferation of the mesenchymal lining of the peritoneum. If the repair process is not completed within a few days, fibroblast proliferation starts which ultimately will end in collagen deposition and adhesion formation. Key players in this process are in particular fibrin and fibrinolysis, macrophages and their secretion products such as growth hormones and cytokines, and obviously the epithelial repair process.

From this repair process it results that. adhesion formation is largely independent from the extent of the trauma.

Prevention of adhesion formation has been attempted mechanically and by modulating the inflammatory reaction. Mechanical adhesion prevention has been attempted by barrier methods and by the instillation of viscous fluids at the end of surgery keeping the surfaces separated, or recently by coating the surfaces by biodegradable gels.

These known approaches have been only moderately successful.

SUMMARY OF THE INVENTION

It is the aim of the present invention to provide a use of a medicament, an endoscopic system, and a method for more effectively preventing adhesion.

Surprisingly, it was found that anoxemia is a major cause and/or cofactor of adhesion formation. The invention relates in particular to the use of an anoxemia preventing compound for the manufacture of a medicament for preventing adhesion formation These local or systemic administered medicaments according to the invention reduce adhesion formation by decreasing anoxemia in particular of the peritonial lining or the consequences of peritoneal anoxemia.

Hereunder mechanisms and drugs are highlighted which are proven to be relevant to reduce/prevent adhesion formation. These drugs have hitherto not been used in adhesion prevention, at least not in the concept of prevention of ischemia and/or anoxemia and/or of the consequences of ischemia and/or anoxemia, and in particular by or during $CO_2$ pneumoperitoneum.

The damage caused by ischemia and/or anoxemia has been investigated to occur during the period of ischemia and/or anoxemia itself, and during the reperfusion period. The mechanisms which are recognized to be involved are Ca channels, kalium efflux, free oxygen radicals, expression of a series of proteins such as VEGF (a potent angiogenic factor), other cytokines which are leucocyte attractants and heat shock proteins.

These drugs can be applied either systemically, or by local instillation during surgery, or by the prolonged administration intraperitoneally postoperatively, preferably locally e.g. by miniosmotic pumps. Experiments have shown, that this is feasible, that the local administration has the advantage that much higher concentrations of active drugs can be obtained, and that the administration for 24 to 36 hours postoperatively is sufficient.

Considering the knowledge of prevention of ischemia and/or anoxemia and/or of the consequences of ischemia and/or anoxemia the time course of administration of these drugs to prevent adhesions will obviously be different from those actually used.

Together with the hereunder explained oxygen/$CO_2$ pneumoperitoneum or independently at least the following mechanisms and/or drugs/mechanisms can be used for the prevention of adhesions:

drugs to prevent anoxemia or the consequences thereof can also be administered, continuously or intermittently in the insufflation gas or mixture as an aerosol. For this purpose all drugs as mentioned later can be used, activation of potassium channels;

modulation of macrophage activation and leucocyte attraction through cytokines, or their inhibitors e.g. IL8, IL6, IL1;

the effect of VEGF expression, a direct consequence of anoxemia, will be blocked by antibodies or other inhibitors;

indomethacin, which can inhibit the membrane lipid peroxidation products following anoxemia;

prostaglandin El was shown to reduce the consequences of ischemia and/or anoxemia in the liver;

allopurinol was shown to reduce the consequences of ischemia and/or anoxemia in the kuppfer cells of the liver through an effect on xanthine-oxidase;

calcium channel blockers, free radical scavengers, lipid peroxysomes, and pregnatrienes;

calcium antagonists;

prevention of hypoxia associated stress proteins;

acidosis can prevent reperfusion damage;

MP, dopamine and ATP-MgCl2 administered following the anoxemia as demonstrated for the liver.

The amount of these active ingredients of the present invention may vary depending on the formulation, but it is usually from 0.1 to 50% by weight irrespective of the manner of administration. The dose is determined taken into consideration the age, sex, and syptom of disease of the subject, the desired therapeutic effect, the period of administration, etc. However preferably a daily dose of the active ingredient is from 0.05 to 100 mg for an adult.

The invention relates also to a novel endoscopic insufflation system with supplying means for $O_2$.

Endoscopy also called minimal access surgery has become widely used over the last years because of clearcut advantages of a decreased postoperative morbidity, less pain and a shorter hospitalization. These procedures require by means of an insufflation system or an irrigation system a distension to permit visualization.

Endoscopic surgery uses, at present, almost exclusively pure carbon dioxide gas ($CO_2$). A standard lesion induced either by $CO_2$ laser (superficial lesion) or by monopolar, or bipolar coagulation, (deeper lesion) cause more adhesions when the duration of the pneumoperitoneum is longer. The amount of adhesions increase with time, at least up to 2 hours. All existing insufflation systems are designed to control gas flow for pure carbon dioxide gas. Since $CO_2$ is highly soluble in water, this gas has almost uniformly been used to induce the pneumoperitoneum, for safety reasons. In cases of accidental gas embolism the solubility in water and the exchange capacity in the lungs is estimated to be possibly of crucial life saving importance.

$CO_2$ irritates the peritoneum, as evidenced by the pain when insufflated without anaesthesia, and by the shoulder pain following endoscopic procedures. This can be explained by the pH changes caused by $CO_2$.

The endoscopic insufflation system according to the invention comprises gas supplying means for a insufflation line, wherein the supplying means are designed to supply gas mixtures comprising $O_2$ and in particular gas mixtures of $O_2/CO_2$. Surprisingly it was found that $O_2$ comprising gas mixtures reduce adhesion formation during or by pneumoperitoneum. Preferably the gas mixture is a $CO_2/O_2$ gas mixture in which gasmixture $O_2$ is preferably present in a volume ratio from 1 to 20% and more preferably from 5 to 20% and most preferably from 5 to 10%. Parameters relevant to the upper limit of the mixing ratio are, among others, the explosiveness and the solubility of oxygen in blood.

Other $O_2$ gas mixtures, for example with $N_2O$ or Helium can also be used as insufflation gases with preventing adhesion formation characteristics according to the invention.

For intra-abdominal endoscopy, the distension medium is generally a gas whereas for organs such as a uterus, both gases and fluids can be used.

An endoscopic insufflation system according to the invention is preferably provided with means for moistening the insufflation gas, for example by means of a sprinkler device.

Drying of peritoneal surfaces has been considered a cofactor in adhesion formation. For this reason as a single measure or together with the prevention of anoxemia using oxygen in the insufflation gas or using drugs to prevent anoxemia or the consequences thereof, it is important that the insufflated gas is moistened in order to prevent dehydration of the peritoneal surfaces Instead of moistening the insufflated gas, a sprinkler system has been devised which intermittently sprays the abdominal cavity. This sprinkler device can be attached to any canula, or preferably to the endoscope: under high pressure a small volume of irrigating fluid is intermittently and automatically sprayed in all directions of the abdominal cavity.

The insufflation system according to the invention will be further illustrated hereunder, on the basis of a number of non limitative embodiments, and with reference to the annexed drawing, wherein FIGS. 1 and 2 are extensively schematised drawings of control means of a prefered embodiment of an insufflator system according to the invention.

During endoscopy or endoscopic surgery, the abdominal cavity generally is or can intentionally be irrigated with a solution such as Ringers lactate or any other physiologic solution. The invention that anoxemia or the consequences thereof should be prevented, will use medicated irrigation fluids. For this purpose any of the substances as described can be used, in order to reduce that anoxemia or the consequences thereof, already during surgery. Alternatively, at the beginning of the surgery, the peritoneal surfaces can be coated with a biodegradable gel, which will prevent the direct contact of $CO_2$ with the peritoneal surface and thus changes in pH and/or anoxemia.

First an overview is given of possible technical solutions to the problem of applying carbon dioxide-oxygen ($CO_2/O_2$) gas mixtures during endoscopical surgery.

The requirements of such an insufflation system according to the invention are those of a pure $CO_2$ insufflator with additionally:

means for controlling the ratio of carbon dioxide-oxygen, which ratio is preferably controlled independently from the gas flow;

means for adjusting the ratio of carbon dioxide-oxygen during the endoscopical surgery (e.g. start the operation with pure carbon dioxide and after a while switch only temporarily to a 50% oxygen mixture);

flow control means for the carbon dioxide-oxygen gas mixture;

all materials in contact with oxygen or the gas mixture shall withstand the chemical effects of $O_2$;

if, at least in a part of the system and temporarily, a high $O_2$ concentration may occur, explosion protection is required.

These modifications required by the handling of $O_2$ are known, per se, from respiration systems.

The initiation of the pneumopericoneum should preferably be done at insufflation pressures below 15 mm Hg and at a flow rate of less than 1L/min. Once the pneumoperitoneum established, the most important factor is the intra-abdominal pressure which should not exceed 30 mm of Hg. The flow rate becomes relatively unimportant.

DESCRIPTION OF PREFERRED EMBODIMENTS

A first embodiment of an insufflation system according to the invention makes use of fixed gas mixtures. One can perform endoscopical surgery using carbon dioxide-oxygen gas mixtures using containers of premixed gases. It is obvious that this solution offers total independability of $CO_2$-$O_2$ ratio from gas flow. Flow control can be obtained using existing equipment. This embodiment has the advantage of its simplicity. The only extra equipment needed are some containers with mixtures of carbon dioxide gas and oxygen with different $CO_2$-$O_2$ ratios and a valve to switch from one mixture to another. This valve can be placed before the gas inlet of existing equipment, or it can be integrated into an apparatus for gas flow control. The valve can be pure mechanical, or electromechanical.

An important limitation of this first embodiment is the fact that it is impossible to continuously vary the carbondioxide-oxygen ratio during an endoscopical operation. Only a number of fixed ratios can be used during an operation. Hereunder are two other embodiments proposed, which can overcome this limitation.

Figure 1:
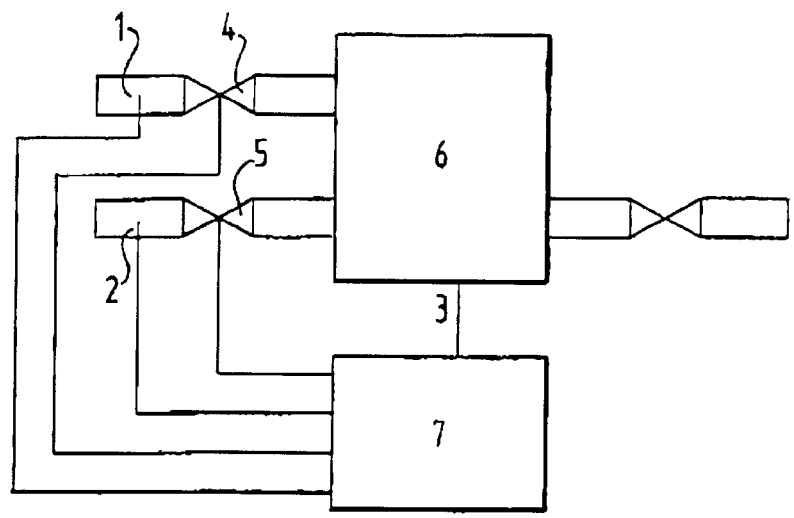
FIG. 1 provides a schematic overview of an open loop control system for mixing carbon dioxide and oxygen in a predefined ratio.

In FIG. 1, the proposed solution consists of a buffer volume 6 and a controller unit 7. The two (one for oxygen, one for carbon dioxide) gas inlets are equipped with electromechanical valves 4 and 5.

A periodically opening of the valves 4 and 5, makes it possible to mix the two gases in the buffer volume 6. If one makes sure that the opening times of the valves are rather small, or the incoming gas flow is rather small or the buffer volume 6 is rather large, then the pressure in the buffer volume 6 will remain rather constant during one period.

In short, the increase in pressure in the buffer volume 6 during one period, can be neglected for small periods, large buffer volumes or small incoming gas flows. By consequence, if these conditions are met, the gas flow in the two gas inlets can be considered equal and the ratio of the two gases in the buffer volume 6 will be the same as the ratio of the opening times of the two valves.

Since no feedback is provided in this solution, some extra measures are necessary to make sure gas always flows in the buffer volume 6 through the valves 3. and 4. This can be achieved by providing the pressure sensors 1, and 3. The controller unit 7 may only periodically open valves if the pressure at sensor 3 is smaller than the pressure at the sensors 1 and 2. The controller unit must issue a warning to the user if the pressure at sensors 1 or 2 drops below some predefined value. In order to compensate for slight differences in input pressure between 1 and 2 (and by consequence, differences in incoming gas flow), the controller must always maintain a predefined pressure difference between the buffer volume 6 and the incoming gas flows.

This embodiment has the advantage of flexibility over the previous one. By varying the ratio of opening times of the valves 4 and 5 any carbon dioxide-oxygen ratio can be achieved. Response will not be immediate, since the buffer volume 6 will introduce a delay, This embodiment can be placed before the gas inlet of existing equipment for flow control, or integrated in new equipment for flow control.

This embodiment tries to overcome the problem of delayed response to different mixture ratios, as discussed above.

Figure 2:
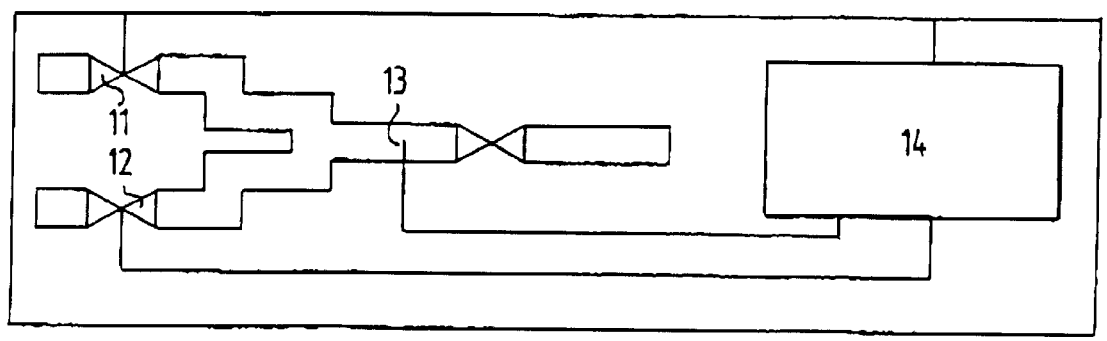
FIG. 2 provides a schematic overview of a third embodiment of the invention with a closed loop control system.

In FIG. 2, the unit 14 measures via the sensor 13 the composition of the gas mixture. It compensates for deviations of a predefined composition by means of the proportional valves 11 and 12 at the gas inlets. This embodiment guarantees a quasi immediate response to a request to alter the mixing ratio. Pressure sensors at the inlets, to guard against a "no pressure", situation at the inlet are no longer necessary, since this must be the case if the controller is no longer able to obtain the requested gas composition. They may be, however, useful in order to build a more efficient controller unit.

Again, this embodiment can be placed before existing equipment for flow control or integrated into new equipment for flow control. It offers the advantages of improved reaction speed and size (no buffer volume needed) to the open loop control system.

It must be stated, however, the above given embodiments are extensively simplified for reasons of clarity, and it is further possible to add some extra sensors for pressure measurement and flow measurement, and if the controller unit is well designed, this system can implement gas mixture and flow control all together, so no extra equipment for flow control will be necessary anymore.

Prevention of anoxemia and of the consequences of anoxemia have been investigated mainly in obstetrics, in cardiology and in transplant surgery. In obstetrics it is obvious that prevention of anoxemia and/or of the consequences of anoxemia are important to prevent brain damage of the child. Also in cardiology prevention of anoxemia and/or of the consequences of anoxemia as a result of ischemia is important to minimize the consequences of an infarction. During transplant surgery (kidney, heart, lung, liver) prevention of ischemia and/or anoxemia and/of of the consequences of ischemia and/or anoxemia is essential to minimize damage of the donor organ.

A lower temperature obviously decreases metabolism and oxygen consumption and has been used to prevent ischemia and/or anoxemia e.g. for the mammary artery transplantation.

A cooled $CO_2$/oxygen mixture will be used to prevent adhesion prevention. The originality of the concept is illustrated by the recent introduction of 2 insufflators with warmed $CO_2$ up to 37°.

The invention further relates to methods for preventing adhesion by controlling anoxemia.

The present invention shows that the presence of $O_2$ diminished the adhesion formation. This was experimentally proven by the administration of 1,2.5,5;10 and 20% of oxygen together with the $CO_2$. In these experiments, exposure of 60 min of pure $CO_2$ increased the adhesion scores 4 fold in comparison with an exposure of 10 min. From a final concentration of 5% oxygen onwards, this adhesiogenic effect of $CO_2$ was completely abolished. Also visually the appearance of the lesions following pure $CO_2$ and following a $CO_2$/oxygen mixture was obviously different, the latter looking much healthier.

These above mentioned experiments demonstrate clearly that prevention of anoxemia reduces adhesion formation by or during $CO_2$ pneumoperitoneum, which principle is used as a basis in developing an insufflation system which delivers a controlled $O_2/CO_2$ mixture.

The invention further relates to a method according to the claims 1–5.

As an illustration of part of the method and of the effectiveness of the method according to claim 1, as an example, in the following a series of experiments in rabbits is described that show that $CO_2$ is an independent adhesiogenic factor. $CO_2$ causes not only pH changes. Taking into account the relative pressures, it was found that the peritoneal lining was anoxic during the pneumoperitoneum, and that this was a direct cause of cell damage and adhesion formation.

$CO_2$ in pneumoperitoneum is generally used because of safety. Indeed the solubility and high exchange rate in the lungs make it the..safest gas available with respect to gas embolism. $CO_2$ pneumoperitoneum has complex systemic and local effects depending on the duration of the application and intraabdominal pressure. Systematic effects of $CO_2$ pneumoperiteum have been described, such as changes in acid-base balance (Moten, M., et al, 1973, Volz, J., et al., 1996), cardiopulmonary system (Barnett, R. B., et al., 1992; Ho, H. S., et al., 1993; Liu, SD. Y., et al., 1991) inmunologic and endocrine systems (Volz, J., et al., 1996). For this reason, other gases have been investigated. Nitrous oxide or air have been used but they are potentially combustible or explosive in presence of cautery (Robinson, J. S., et al., 1975; Esposito, J. M., 1975; El-Minawi, M. F., et al., 1981). Helium is physiologically inert, nonexplosive but it is very expensive (Leighton, T. A., et al., 1992; Bongard, F. S., et al., 1993; Rademaker, B. M., et al., 1995). Locally, the $CO_2$ pneumoperitoneum produces disturbances of the peritoneal surface. It was clinically demonstrated chat $CO_2$ pneumoperitoneum produces intense intraperitoneal acidosis (Volz, J., et al., 1997). Moreover, $CO_2$ exposure may have adverse effects on peritoneal microcirculation and cell-protective systems (Buhur, A., et al., 1997).

Our observation that $CO_2$ pneuoperitoneum increases adhesion formation, could be explained by acidosis or by local anoxemia. To test the latter hypothesis, experiments were carried out with variable $O_2$ concentrations.

Materials and methods

Experimental design:

All animals received two standard $CO_2$ laser injuries. A non opposing lesion was inflicted in the retro-uterine space, i.e. on the posterior utero-vaginal wall, consisting of a 2 $cm^2$ vaporization of the superficial layers with $CO_2$ laser. In addition, an apposing lesion was performed in the oviduct and pelvic side wall, consisting of a 2 $cm^2$ vaporization, on both sides. The time required to induce the lesions varied from 3 to 7 minutes.

Animals were assigned randomly on a daily base, to one of the following seven experimental groups. First and second groups were considered control groups. In group 1, using conventional $CO_2$ pneumoperitoneum, the total duration of the procedure was restricted to 10 minutes. In group 2, the pneumoperitoneum was maintained for 70 minutes, to demonstrate the effect of $CO_2$ pneumoperitoneum. In groups 3, 4, 5, 6 and 7, duration of pneumoperitoneum was also 70 minutes, but the pneumoperitoneum was maintained with a mixture of $CO_2$ and increasing amounts of $O_2$ (1%, 2.5% 5%, 10% and 20%, for groups 3, 4, 5, 6 and 7 respectively).

Adhesions were evaluated by laparoscopy after one week. All second look laparoscopies were videotaped, and subsequently scored blindly by two investigators, taking into account extent (0 to 4 points), type (0 to 3 points), tenacity (0 to 3 points) and inflammatory reaction (0 to 3 points) at the injury and at de-novo siteds.

Animals and surgical procedures:

Sixty five New Zealand white rabbits weighing between 2150 and 3000 grams were operated with a standard puncture laparoscopy. Standard surgical injuries were inflicted with $CO_2$ laser (Sharplan 1060: Sharplan, Tel Aviv, Israel) with a spot diameter of 1 mm and a power setting of 10 watts in the continuous superpulse mode. Pneumoperitoneum was created and maintained with two Thermoflators™ (Karl Storz-Endoscope, Belgium), one for $CO_2$ and one for $O_2$. The output of both insufflators was mixed in a mixing chamber, humidified and warmed. The insufflation pressure was 10 cm of water and the intraabdominal flow rate 20 1/min. It is obvious that all means in contact with $O_2$ are adapted therefor.

Results

Figure 3:
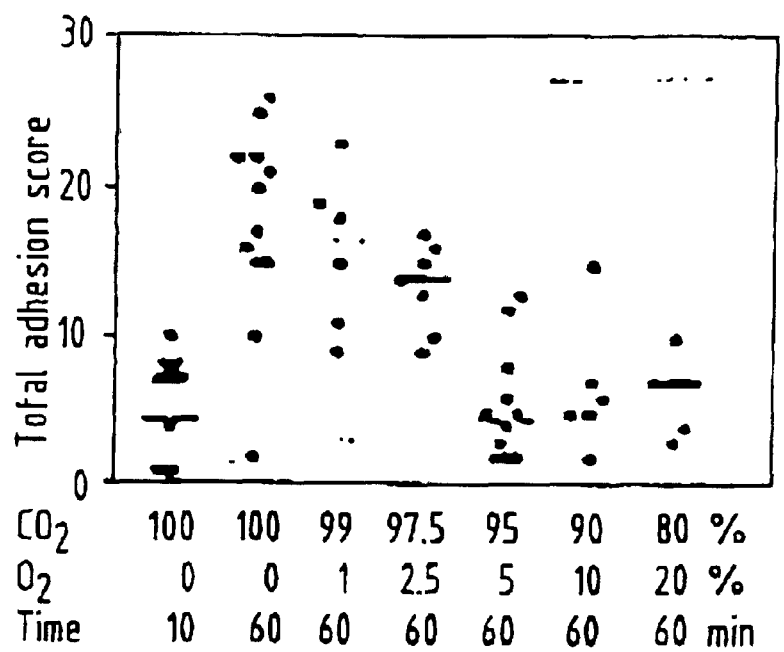
FIG. 3 provides a comparison of total adhesion scores versus time, and $CO_2$, and $O_2$ concentrations.
Figure 3:
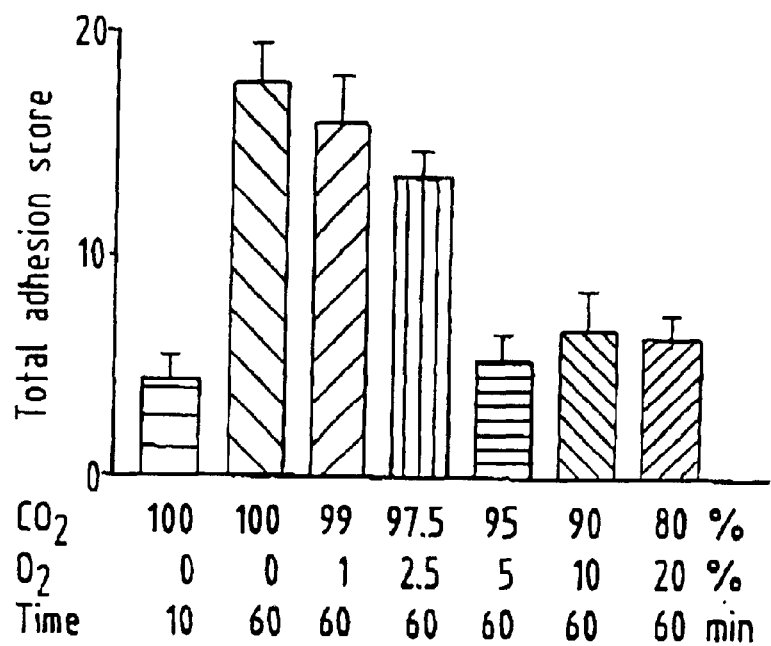

Results are summarized in table 1 and FIG. 3. Adhesion score was higher in group 2 than in group 1 confirming the effect of $CO_2$. Using increasing concentrations of oxygen, the amount of adhesions decreased progressively.

TABLE 1

Differences in total adhesion score between the groups 1, 3, 4, 5, 6 and 7 and the control group with 100% of $CO_2$ (Group 2).

| | Total adhesion score in the experimenial groups 1, 3, 4, 5, 6 and 7 | | | | | |
|---|---|---|---|---|---|---|
| | 10' $CO_2$ | 60' 1% $O_2$ | 60' 2.5% $O_2$ | 60' 5% $O_2$ | 60' 10% $O_2$ | 60' 20% $O_2$ |
| 60' $CO_2$ | P = 0.0002 | P = NS | P = 0.05 | P = 0.0005 | P = 0.007 | P = 0.005 |

Groups 2 and 3 presented higher total adhesion scores (mean 17.5±6.7 and 15.8±5.2 for groups 2 and 3 respectively, P=NS). Mean total adhesion scores for 5%, 10% and 20% of oxygen concentration (5.3±3.8, 6.6±4.4, 6.3±2.5, respectively) was comparable with the control group 1, consisting in only 10 minutes procedure (4.5±3.7, P=NS). (FIG. 3).

Figure 4:
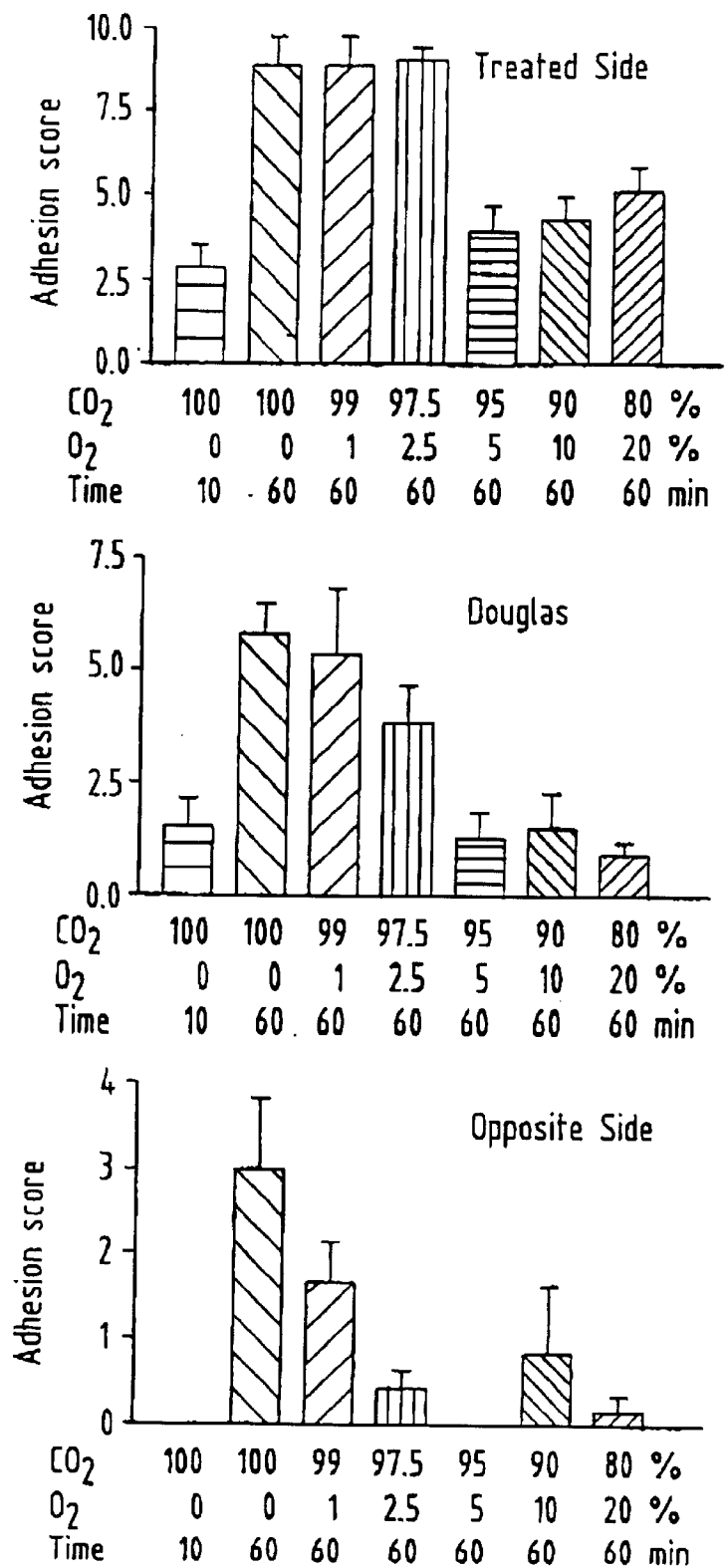
FIG. 4 provides a comparison of adhesion scores versus time and $CO_2$, and $O_2$ concentrations at the lesion sites, non opposing lesion, and de novo adhesions.

This decrease in total adhesion score with the addition of $O_2$ was not only observed at the lesion sites, i.e. opposing lesion in tube/side wall (P=0.0014) and non opposing lesion in the pouch of Douglas (P=0.0002), but also de novo adhesions around the opposite tube (P=0.0001) (FIG. 4).

Figure 5:
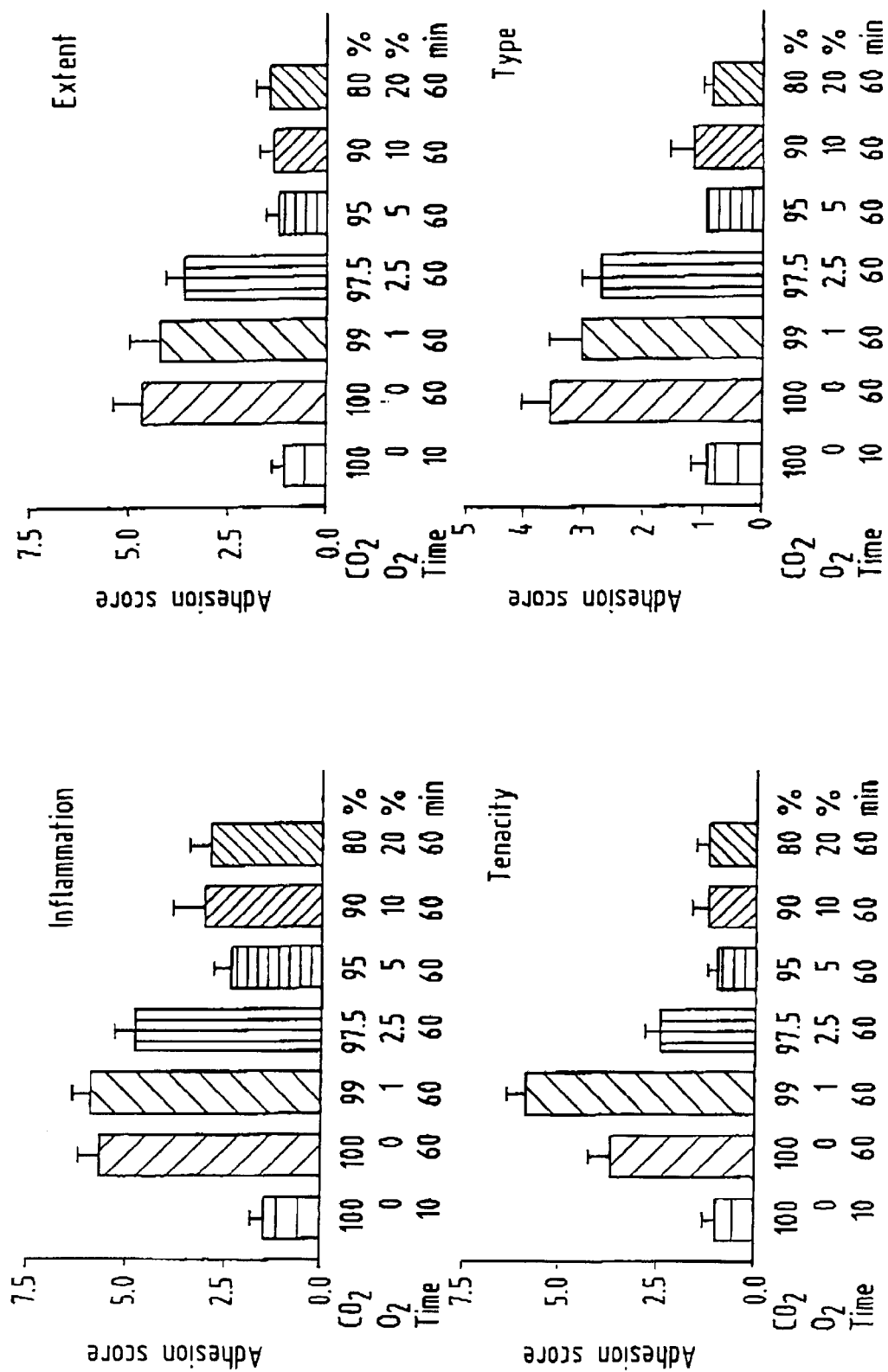
FIG. 5 provides a comparison of adhesion scores versus time and $CO_2$, and $O_2$ concentrations based on inflammation, extent, tenacity, and type.

Moreover, this reduction in total score was obviously produced by a reduction in all items of the scoring system, such as inflammation, extent, tenacity and type (FIG. 5).

Laparoscopic surgery requires a pneumoperitoneum to provide adequate space to work. $CO_2$ gas is the most common distending medium in laparoscopic surgery because its high solubility and exchange rate in the lungs. $CO_2$ absorbed across the peritoneal surface can cause systematic effects such as respiratory acidosis, hypercarbia and arrhytmia. Locally, $CO_2$ induces severe acidosis and some anoxemia in the periconeal surface. These disadvantages of $CO_2$ pneumoperitoneum have led investigators to look for other gases. Nitrous oxide and air have been tested but they can be dangerous in presence of cautery. Gasless laparoscopy is another alternative. The disadvantage is a more difficult surgical procedure, since the visceras can interfere with a good visualization. Helium is nonexplosive, inert and nontoxic but is expensive. Our data suggest that the addition of oxygen is useful in the preventing of adhesion formation.

What is claimed is:

1. A method of treating or preventing adhesion formation following a surgical procedure comprising administering to a patient in need thereof a medicament comprising a gas mixture comprising $O_2$ wherein the $O_2$ is present in a volume ratio of from 1 to 20% and in an amount effective to treat or prevent adhesion.

2. The method of claim 1, wherein the procedure is $CO_2$ pneumoperitoneum.

3. The method of claim 1, wherein the gas mixture is an $O_2/CO_2$ gas mixture.

4. The method of claim 1, wherein the $O_2$ is present in a volume ratio of from 5 to 20%.

5. The method of claim 1 further comprising administering to the patient at least one medicament selected from the group consisting of potassium channels; modulators of macrophage activation and leucocyte attraction through cytokines, or their inhibitors, antibodies or inhibitors blocking the effect of VEGF expression; prostaglandin E1; allopurinol; calcium channel blockers; free radical scavengers; lipid peroxysomes; pregnatrienes; calcium antagonists; hypoxia; acidosis; MP; dopamine; and ATP-$MgCl_2$.

6. Endoscopic insufflation system having an insufflation line comprising gas supplying means wherein the supplying means supply a gas mixture comprising $O_2$ in a volume ratio of from 1 to 20% and in an amount effective to treat or prevent adhesion formation in a patient following a surgical procedure and further comprising means for moistening the insufflation gas, means for the control of the temperature of the gas, or both.

7. Endoscopic insufflation system of claim 6, wherein the $O_2$ is present in a volume ratio of from 5 to 20%.

8. The endoscopic insufflation system of claim 6, further comprising ratio means to control the ratio in the gas mixture.

9. Endoscopic insufflation system of claim 8, wherein the gas mixture is an $O_2/CO_2$ gas mixture and the ratio means controls the ratio of a $O_2/CO_2$ gas mixture.

* * * * *